United States Patent [19]

Rüegger et al.

[11] 4,210,581
[45] * Jul. 1, 1980

[54] ORGANIC COMPOUNDS

[75] Inventors: Artur Rüegger, Bottmingen; Max Kuhn, Basel, both of Switzerland

[73] Assignee: Sandoz Ltd., Basel, Switzerland

[*] Notice: The portion of the term of this patent subsequent to Aug. 22, 1995, has been disclaimed.

[21] Appl. No.: 914,118

[22] Filed: Jun. 9, 1978

Related U.S. Application Data

[63] Continuation-in-part of Ser. No. 736,106, Oct. 27, 1976.

[30] Foreign Application Priority Data

Nov. 4, 1975 [CH] Switzerland .................. 14195/75

[51] Int. Cl.² .............. C07C 103/52; A61K 37/00; C07D 210/00
[52] U.S. Cl. .................. 260/112.5 R; 260/239.3 R; 424/177
[58] Field of Search .............. 424/177; 260/112.5 R, 260/239.3 R

[56] References Cited

U.S. PATENT DOCUMENTS 4,108,985  8/1978  Ruegger et al. .................. 424/177

*Primary Examiner*—Delbert R. Phillips
*Attorney, Agent, or Firm*—Gerald D. Sharkin; Robert S. Honor; Thomas O. McGovern

[57] ABSTRACT

The present invention provides cyclosporin C which can be hydrogenated to produce dihydrocyclosporin C of formula, useful as an immunosuppressive.

3 Claims, 2 Drawing Figures

ORGANIC COMPOUNDS

This is a continuation-in-part of our copending application Ser. No. 736,106 filed Oct. 27, 1976.

The present invention relates to cyclosporins.

The present invention provides the compound dehydrocyclosporin C of formula I,

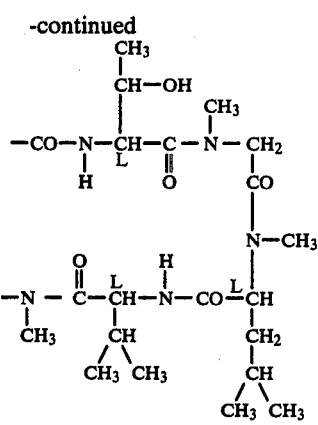

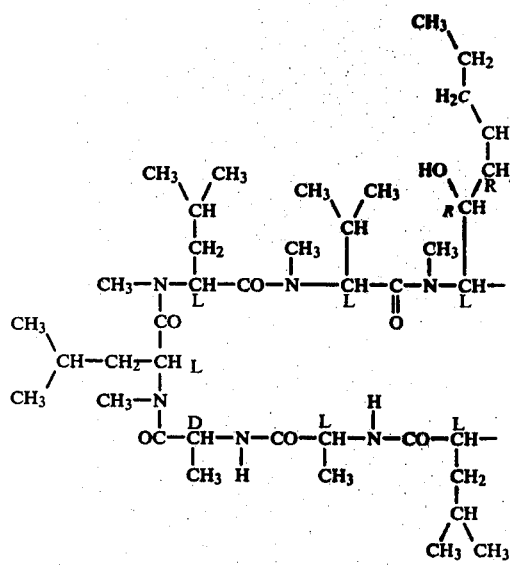

The present invention provides a process for the production of dihydrocyclosporin C by hydrogenation of cyclosporin C of formula II,

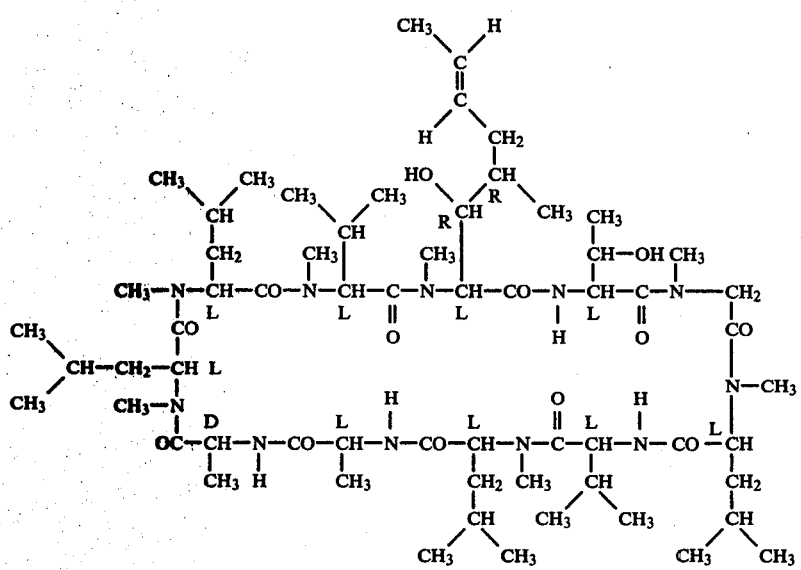

Dihydrocyclosporin C has the following characteristics:

M.Pt. 160°–162° C. (amorphous), slightly hygroscopic.

$[\alpha]_D^{20} = -242°$ (c=0.5 in CHCl$_3$)
= $-174.5°$ (c=0.5 in CH$_3$OH).

U.V. spectrum (CH$_3$OH)—end absorption

Figure 1:
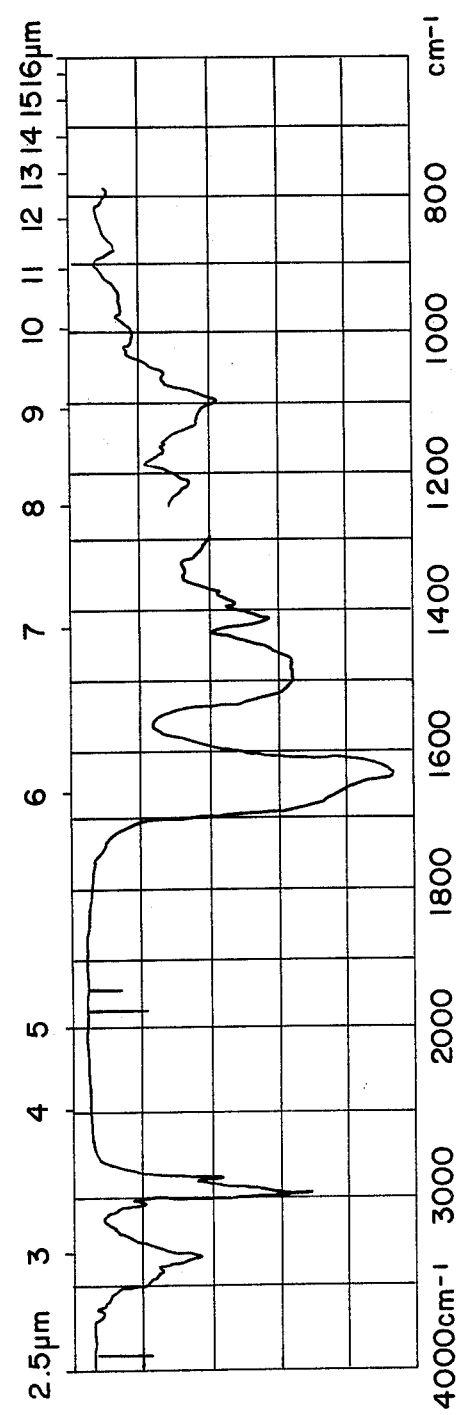

I.R. spectrum (CH$_2$Cl$_2$)—see FIG. 1

Figure 2:
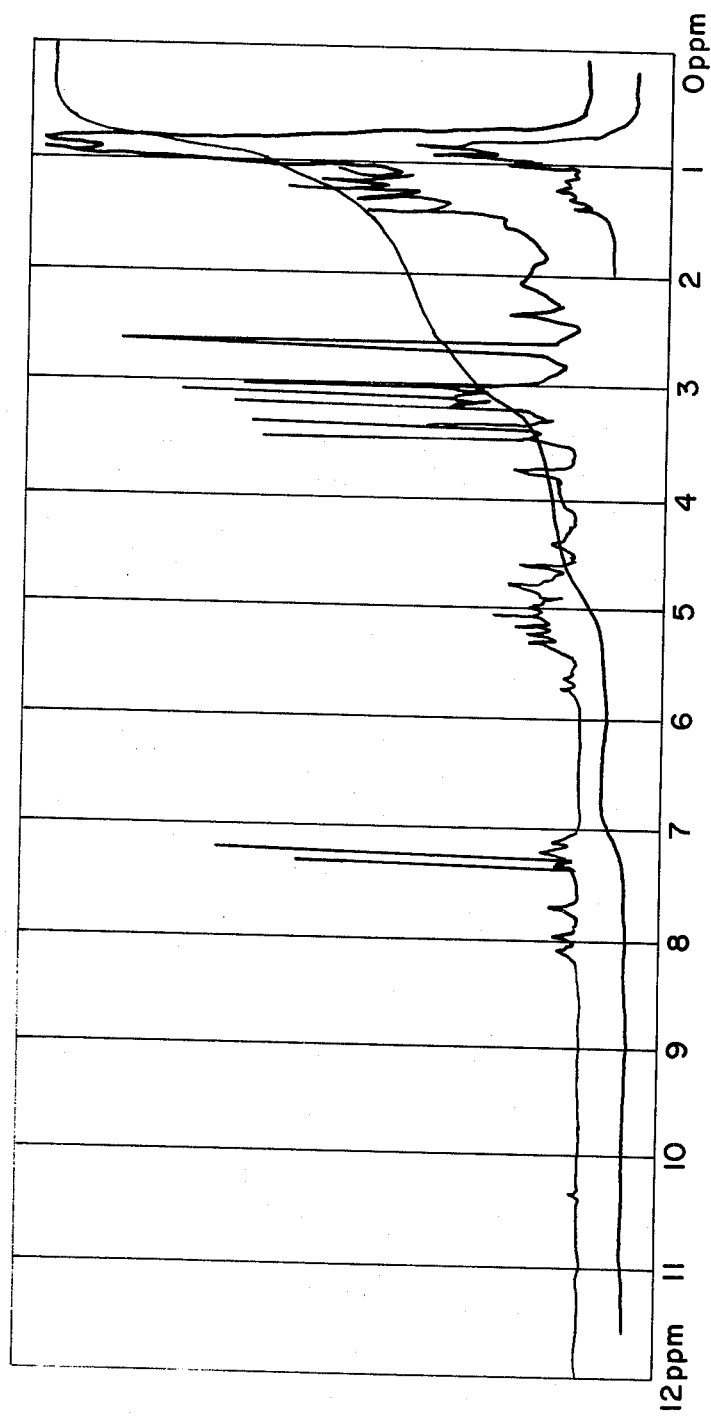

NMR spectrum at 90 MHz (CDCl$_3$)—see FIG. 2 (tetramethylsilane as internal standard; the signals at 7.23 and 7.33 ppm are due to trace amounts of CHCl$_3$ and C$_6$H$_6$ respectively).

Analysis Calc. for C$_{62}$H$_{113}$N$_{11}$O$_{13}$: C 61.0%; H 9.3%; N 12.6%; O 17.0%. Found: C 61.1%; H 9.6%; N 12.4%; O 17.3%.

SOLUBILITY

Dihydrocyclosporin C at room temperature is easily soluble in benzene, dichloromethane, chloroform, ehtyl acetate, acetone, ethanol and methanol, and is difficulty soluble in water.

| T.l.c. ("Merck" Silica-gel 60 F-254) | |
| --- | --- |
| Eluant | R$_f$-value |
| Chloroform-methanol (94:6) | 0.40 |
| Acetone | 0.66 |
| Acetone-hexane (1:1) | 0.38 |
| Acetone-chloroform (1:1) | 0.42 |

The spots may be detected in conventional manner, e.g. with iodine.

The process may be effected in conventional manner for such hydrogenation reactions, e.g. by catalytic hydrogenation.

Suitable solvents include ethyl acetate or lower aliphatic alcohols, e.g. methanol, ethanol or isopropanol. The hydrogenation is conveniently effected under neutral conditions between 20° and 30° C. at atmospheric pressure or slightly elevated pressures. Suitable catalysts include platinum, preferably palladium, e.g. palladium on charcoal.

The resultant hydrogenation product may be purified in known manner, e.g. by chromatography.

The starting material, cyclosporin C, may be obtained by cultivating a cyclosporin C-producing strain of the fungi species Trichoderma polysporum (Link ex Pers) Rifai or Cylindrocarpon lucidum Booth an isolating Cyclosporin C from the resultant culture broth.

The cultivation may be effected in known manner (see for example D.O.S. No. 2,455,859), preferably using strain NRRL 5670 or 8044 deposited at the United States Department of Agriculture depository (Northern Research and Development Division) Peoria Ill., U.S.A.

Cyclosporin C may be isolated by chromatography as a compound active against Aspergillus Niger and having greater polarity than Cyclosporins A and B (designated S7481/F-1 and S7481/F-2 in the above mentioned D.O.S.).

It will be appreciated that by virtue of the various functional groups present in cyclosporin C it is a useful intermediate for the preparation of a wide variety of compounds, e.g. dihydrocyclosporin C.

In the following Example all temperatures are in degrees Centigrade.

EXAMPLE 420 mg of palladium on charcoal (10% palladium) in 40 ml ethanol are prehydrogenated for 75 minutes. To the resultant suspension of catalyst is added a solution of 8.53 g of Cyclosporin C in 110 ml ethanol. The mixture is hydrogenated at 20° at a pressure of 736 mm mercury until the uptake of hydrogen has ceased. The catalyst is filtered off and the filtrate is evaporated to dryness at 20° to 40°. The residue is chromatographed on a column of 1 kg silicagel "Merck" (size—0.06-0.2 mm diameter). Elution with chloroform/methanol (97.5:2.5) affords after combination of the pure fractions, white amorphous dihydrocyclosporin C which is dried in a high vacuum at 55° for 6 hours. To remove water the product is taken up in benzene and evaporated in a vacuum at 30° to 50°. The procedure is repeated twice more, with final drying at 55° (2 hours) and then 80° (2 hours) in a high vacuum.

The starting material Cyclosporin C is obtained as follows:

400 liters of a culture broth obtained by aerobic submersion cultivation of the strain NRRL 8044 of Trichoderma polysporum (Link ex Pers) Rifai [see Example 3 of D.O.S. No. 2,455,859] is extracted by stirring with 400 liters of n-butyl acetate. After separation in a Westfalia-Separator, the organic phase is concentrated in a vacuum and the crude extract is defatted by a three stage extraction between petroleum ether and methanol/water (9:1). The resultant material is dissolved in chloroform and chromatographed on 4.5 kg silicagel 60 "Merck" (diameter 0.2 to 0.5 mm), using chloroform with increasing amounts of methanol as eluant, Chloroform+1.5% methanol elutes Cyclosporins A and B, and chloroform+3% methanol elutes Cyclosporin C. [The Cyclosporin C may be detected using t.l.c. on silica gel foils "Polygram" using chloroform/methanol 95:5 as eluant, Rf values - Cyclosporin A 0.44; B 0.37; C 0.26].

After combination and evaporation of the eluant fractions containing Cyclosporin C, the chromatographic purification is repeated. The Cyclosporin C containing fractions are collected and evaporated at 20°-40°. The residue is treated with 10 times its weight of a mixture of alcohol containing 5% per weight of active charcoal. After filtration the mixture is evaporated at 20° to 40° in a vacuum and then dried in a high vacuum at 55° C.

Final purification comprises dissolving the resultant residue in a 5 times amount of ether and by the slow addition of a 30 times about of hexane. On shaking a solid substance precipitates and is collected after cooling of the mixture at 0° to 5°. This is washed with cold hexane and dried at 55° in a high vacuum. From a 2.5 times amount of acetone the residue affords at −15° colourless, prismatic needles of crystalline Cyclosporin C.

M.Pt.=152°-155°.

$[\alpha]_D^{20} = -255°$ (c=0.5; CHCl$_3$)

$[\alpha]_D^{20} = -182°$ (c=0.5; CH$_3$OH)

Dihydrocyclosporin C is useful because it exhibits pharmacological activity in animals. In particular, dihydrocyclosporin C exhibits a stimulatory effect in humoral immunity, and an immunosuppressive activity in cellular immunity, as indicated in standard tests, e.g. those described in J. F. Borel et al, Agents and Actions 6, 468-475 (1976), viz:

(i) in the Jerne test the effect of the substance on local hemolysis in gel is observed. A significant stimulation of hemolytic plaque-forming cells, such as immunoglobulin M and G$_{2a}$ antibodies, is obtained at a dose of 50 to 200 mg/kg per os. animal body weight of mice;

(ii) in the hemagglutination test (HAT) in mice a stimulation of the antibodies formed against sheep erythrocytes is obtained at a dose of from 100 to 200 mg/kg per os. animal body weight;

(iii) in the skin transplantation (allograft) test in mice a significant prolongation in the period of survival of skin grafts in H-2 histoincompatible mice is observed at a dose of from 100 to 200 mg/kg per os. animal body weight;

(iv) in the experimental allergic encephalomyelitis (EAE) test in rats the incidence of paralysis induced by experimentally induced nerve tissue damages is reduced significantly at a dose of between 50 and 100 mg/kg/day;

(v) in the oxazolone skin hypersensitivity reaction in mice a significant and pronounced inhibition of swelling is obtained (suppressive index 0.48 to 0.63) with doses of 70 to 200 mg/kg;

Dihydrocyclosporin C is therefore useful for the suppression of the proliferation of lymphocytes, and is therefore useful in the treatment of autoimmune diseases, suppressing the rejection of transplants, e.g. organ transplants such as skin, bone narrow and kidney transplants, as well as post-infectious encephalomelitis and multiple sclerosis.

Furthermore dihydrocyclosporin C is useful as an agent for the treatment of chronic inflammations and polyarthritis, as indicated by an inhibition of swellings in the Freund adjuvant arthritis latent period test in rats on p.o administration of from about 1 to about 10 mg/kg.

For the above mentioned uses the dosage will, of course, vary depending on the compound employed, mode of administration and therapy desired. However, in general, satisfactory results are obtained when administered at a daily dosage of from 1 to about 200 mg per kg animal body weight, conveniently given in divided doses 2 to 4 times a day or in sustained release form. For the larger mammal, the total daily dosage is in the range from about 50 to about 1000 mg, and dosage forms suitable for oral administration comprise from about 12 mg to about 500 mg of the compound admixed with a solid or liquid pharmaceutical carrier or diluent.

The present invention also provides a pharmaceutical composition comprising dihydrocyclosporin C in association with a pharmaceutical carrier or diluent. Such compositions may be formulated in conventional manner so as to be, for example, a solution or a tablet.

What is claimed is:

1. Cyclosporin C of formula,

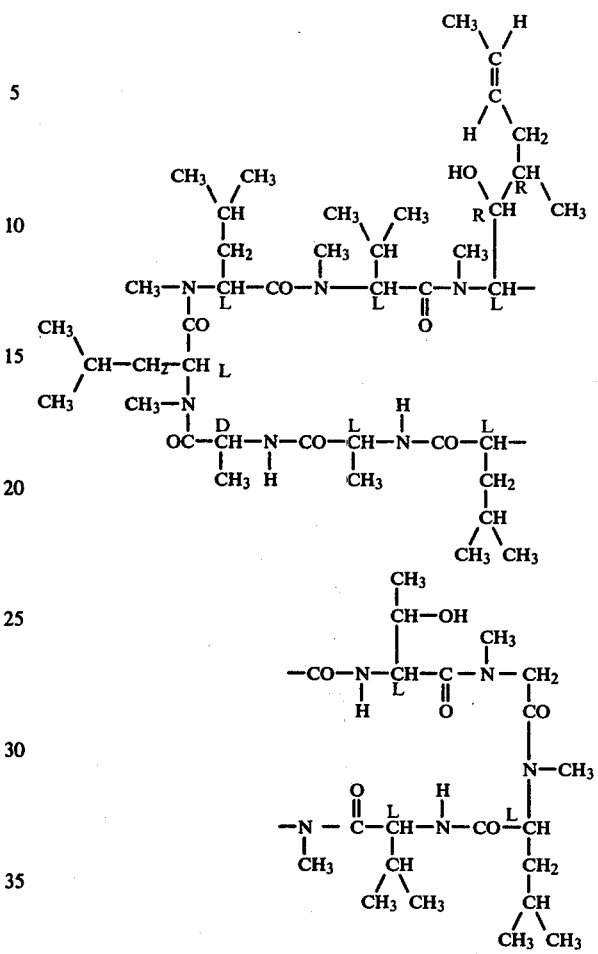

2. A compound of claim 1 in crystalline form.
3. Cyclosporin C substantially free from cyclosporin A.

* * * * *

UNITED STATES PATENT AND TRADEMARK OFFICE
CERTIFICATE OF CORRECTION

PATENT NO. : 4,210,581                          Page 1 of 3

DATED : July 1, 1980

INVENTOR(S) : Artur Rüegger/Max Kuhn

It is certified that error appears in the above—identified patent and that said Letters Patent is hereby corrected as shown below:

In the formula of the Abstract and in Columns 1 and 2 (formula I); delete the formula and insert in its place the formula

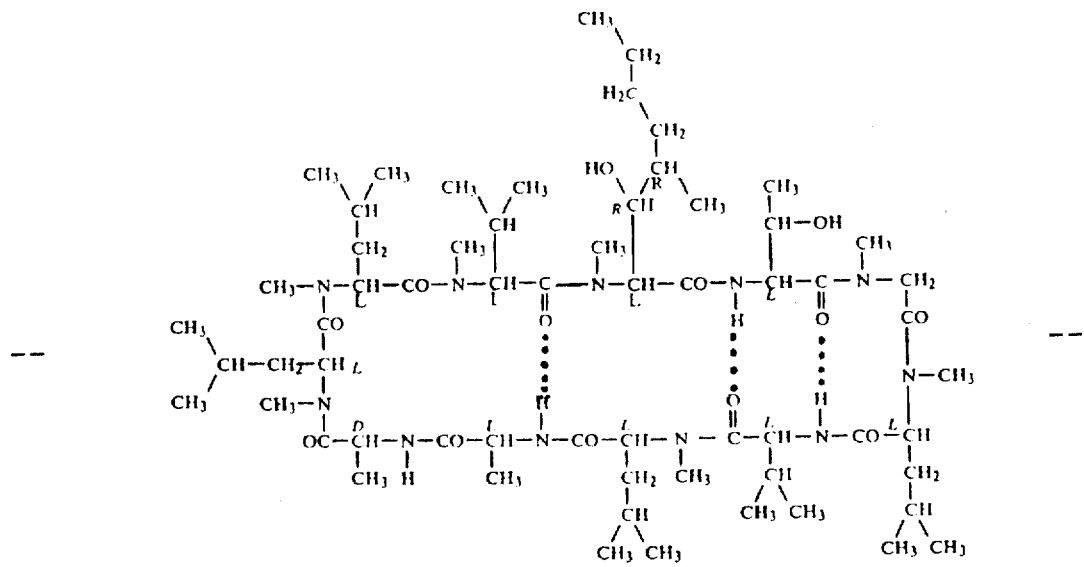

UNITED STATES PATENT AND TRADEMARK OFFICE
CERTIFICATE OF CORRECTION

PATENT NO. : 4,210,581       Page 2 of 3
DATED      : July 1, 1980
INVENTOR(S): Artur Rüegger/Max Kuhn It is certified that error appears in the above—identified patent and that said Letters Patent is hereby corrected as shown below:

Column 2 (formula II) and Column 6 (Claim 1); delete the formula and insert in its place the formula

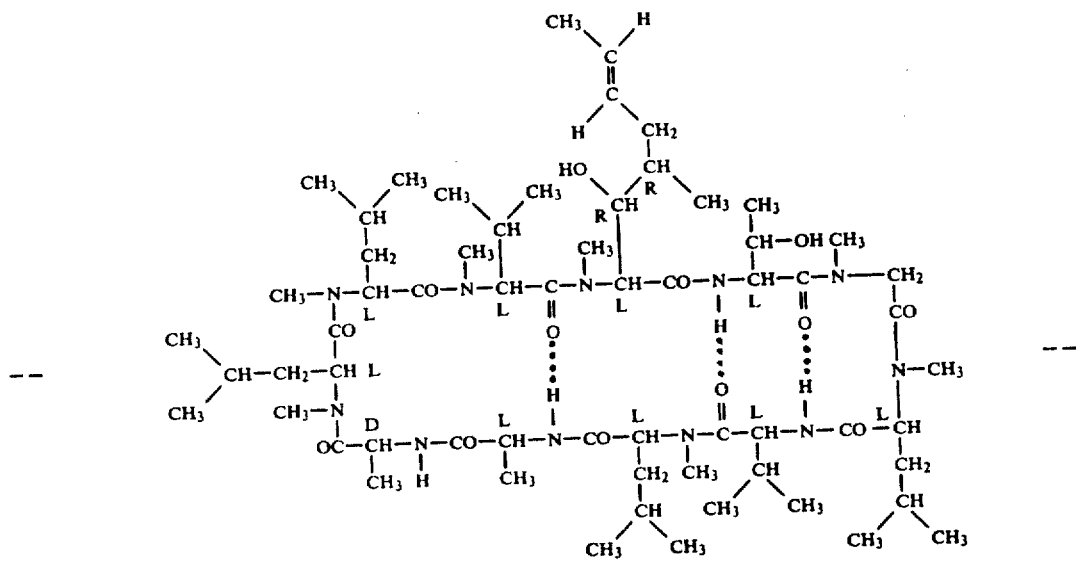

UNITED STATES PATENT AND TRADEMARK OFFICE
CERTIFICATE OF CORRECTION

PATENT NO. : 4,210,581

DATED : July 1, 1980

INVENTOR(S) : Artur Rüegger/Max Kuhn

It is certified that error appears in the above—identified patent and that said Letters Patent is hereby corrected as shown below:

Column 1, line 7, delete the word "dehy-" and insert in its place the word -- dihy- --.

Column 2, line 66; delete the word "ehtyl" and insert in its place the word --ethyl--.

Column 3, line 26; delete the word "an" and insert in its place the word --and--.

Column 4, line 14; after the word "eluant" delete the comma and insert in its place a period.

Column 4, line 26; delete the word "about" and insert in its place the word --amount--.

Column 4, line 26; after the word "shaking" insert a comma.

Signed and Sealed this

Eighth Day of June 1982

|SEAL|

*Attest:*

*Attesting Officer*

GERALD J. MOSSINGHOFF

*Commissioner of Patents and Trademarks*